US011267723B2

(12) United States Patent
Anderson et al.

(10) Patent No.: US 11,267,723 B2
(45) Date of Patent: Mar. 8, 2022

(54) METHOD OF PURIFYING METAL OXIDE PARTICLES AND USES THEREOF

(71) Applicant: Royal Melbourne Institute of Technology, Melbourne (AU)

(72) Inventors: Amanda Anderson, Eltham (AU); Vipul Bansal, Heidelberg West (AU); Jos Laurie Campbell, Mountain View, CA (US); Rajesh Ramanathan, Malvern East (AU); Jyoti Arora, Ringwood (AU); Ravi Shukla, Rosanna (AU)

(73) Assignee: Royal Melbourne Institute of Technology, Melbourne (AU)

( * ) Notice: Subject to any disclaimer, the term of this patent is extended or adjusted under 35 U.S.C. 154(b) by 34 days.

(21) Appl. No.: 16/333,691

(22) PCT Filed: Sep. 8, 2017

(86) PCT No.: PCT/AU2017/050981
§ 371 (c)(1),
(2) Date: Mar. 15, 2019

(87) PCT Pub. No.: WO2018/049468
PCT Pub. Date: Mar. 22, 2018

(65) Prior Publication Data
US 2019/0225491 A1    Jul. 25, 2019

(30) Foreign Application Priority Data

Sep. 15, 2016    (AU) ................................ 2016903721

(51) Int. Cl.
*C01G 1/02* (2006.01)
*C01G 49/02* (2006.01)
*C01G 49/08* (2006.01)
*B01D 21/01* (2006.01)
*H01F 1/11* (2006.01)
(Continued)

(52) U.S. Cl.
CPC .............. *C01G 49/02* (2013.01); *A61K 49/06* (2013.01); *A61K 49/1818* (2013.01);
(Continued)

(58) Field of Classification Search
CPC .......... C01G 49/02; C01G 49/08; C01G 1/02; B01D 21/01; H01F 1/11
See application file for complete search history.

(56) References Cited

U.S. PATENT DOCUMENTS 8,771,699 B2 *   7/2014   Waldoefner ........... C01G 49/02
                                                    424/178.1
10,450,199 B2 *  10/2019  Hemgesberg .......... C01G 35/00
(Continued)

FOREIGN PATENT DOCUMENTS

CN    103316614 A    9/2013
JP    2004-043287 A  2/2004
(Continued)

OTHER PUBLICATIONS

Farrell etal," Preparation and Characterization of Monodisperse Fe Nanoparticles", J. Phys. Chem. B 2003, 107, 40, 11022-11030 (Year: 2003).*
(Continued)

*Primary Examiner* — David M Brunsman
(74) *Attorney, Agent, or Firm* — Wolf, Greenfield & Sacks, P.C.

(57) ABSTRACT

A method of purifying a plurality of metal oxide particles produced from a synthesis process comprising the step of washing a plurality of metal oxide particles in a first solvent composition comprising of at least one aliphatic ether, and at least one flocculant. In one embodiment, the plurality of metal oxide particles are iron oxide particles produced from a thermal decomposition synthesis process between an iron-oleate complex and oleic acid in 1-octadecene, wherein the
(Continued)

first solvent composition comprises a 1:1 (vol/vol) ratio of an aliphatic ether in the form of diethyl ether and a flocculant in the form of methanol. The washed iron oxide particles are further washed in a second solvent composition comprising a 1:1 (vol/vol) ratio of hexane and ethanol, and then finally dispersed in hexane. The resulting iron oxide particles find use as a contrast agent for magnetic resonance imaging (MRI) or as magnetic particles in magnetic separation, magnetism-directed targeting or magnetism-induced heating.

19 Claims, 9 Drawing Sheets

(51) Int. Cl.
 *A61K 49/06* (2006.01)
 *A61K 49/18* (2006.01)
 *B03C 1/01* (2006.01)
 *B03D 3/06* (2006.01)
 *C01B 13/16* (2006.01)

(52) U.S. Cl.
 CPC ............... B01D 21/01 (2013.01); B03C 1/01 (2013.01); B03D 3/06 (2013.01); C01G 1/02 (2013.01); C01G 49/08 (2013.01); H01F 1/11 (2013.01); *C01B 13/16* (2013.01); *C01P 2002/82* (2013.01); *C01P 2004/04* (2013.01)

(56) References Cited

U.S. PATENT DOCUMENTS

| | | | |
|---|---|---|---|
| 10,624,976 B2 * | 4/2020 | Begin-Colin | ........... A61P 35/00 |
| 2005/0191231 A1 | 9/2005 | Sun | |
| 2006/0275201 A1 * | 12/2006 | Niederberger | ......... C01G 33/00 |
| | | | 423/593.1 |
| 2008/0138262 A1 | 6/2008 | Brooks et al. | |
| 2008/0203351 A1 * | 8/2008 | Gao | ........................ B22F 9/30 |
| | | | 252/62.51 R |
| 2013/0220178 A1 * | 8/2013 | Zieba | ..................... C01G 37/02 |
| | | | 106/287.17 |

FOREIGN PATENT DOCUMENTS

| | | | |
|---|---|---|---|
| JP | 2010-512463 A | 4/2010 | |
| JP | 2013-534893 A | 9/2013 | |
| JP | 2015-171700 A | 10/2015 | |
| WO | WO 2012/018240 A2 | 2/2012 | |
| WO | WO-2013085574 A1 * | 6/2013 | ............. C01B 33/18 |

OTHER PUBLICATIONS

International Search Report and Written Opinion for International Application No. PCT/AU2017/050981, dated Oct. 20, 2017.
Hu et al., Preparation of magnetite nanocrystals with surface reactive moieties by one-pot reaction. Journal of Colloid and Interface Science. Jul. 15, 2007;311(2):469-74.
Jia et al., Gelification: an effective measure for achieving differently sized biocompatible Fe3O4 nanocrystals through a single preparation recipe. Journal of the American Chemical Society. Nov. 1, 20114;133(48):19512-23.
Li et al., Preparation of water-soluble magnetite nanocrystals from hydrated ferric salts in 2-pyrrolidone: mechanism leading to Fe3O4. Angewandte Chemie International Edition. Jan. 2005;44(1):123-6.
Extended European Search Report for European Application No. 17849916.6, dated May 12, 2020.
EP17849916.6, May 12, 2020, Extended European Search Report.

* cited by examiner

METHOD OF PURIFYING METAL OXIDE PARTICLES AND USES THEREOF

RELATED APPLICATIONS

This application is a national stage filing under 35 U.S.C. § 371 of international application number PCT/AU2017/050981, filed Sep. 8, 2017, which claims the benefit of Australian application number AU 2016903721, filed Sep. 15, 2016.

TECHNICAL FIELD

The present invention relates broadly to a method of purifying metal oxide particles produced from a synthesis process, and uses thereof. More particularly, the present invention relates to a method of purifying a plurality of iron oxide particles produced from a thermal decomposition synthesis process so that the purified iron oxide particles may be used for biomedical and/or other consumer-based applications.

The following discussion of the background to the invention is intended to facilitate an understanding of the invention. However, it should be appreciated that the discussion is not an acknowledgement or admission that any of the material referred to was published, known or part of the common general knowledge in Australia or any other country as at the priority date of any one of the claims of this specification.

BACKGROUND OF THE INVENTION

Over the last decade there has been much attention directed towards producing magnetic (nano) particles for a range of biomedical applications such as therapeutics, biosensing, cell separation and staining, and magnetic resonance imaging (MRI).

Iron oxide particles with different magnetic properties can be produced according to known literature methods. However, the purity of the iron oxide particles produced according to these methods leaves much to be desired, which renders them unsuitable for many of the biomedical applications highlighted above.

The cleaning or purification procedures outlined in these known literature methods are not well described. In many cases, regardless of the synthesis method used to produce the iron oxide particles, the cleaning or purification procedure typically involves washing the as-produced particles with copious amounts of a low order alcohol to remove the excess reagents and/or undesirable by-products associated with the synthesis method employed.

For example, one of the most commonly used methods for the production of iron oxide particles is the thermal decomposition technique because of the advantages associated with this technique such as monodispersity and high crystallinity of the obtained particles post-synthesis. In the last part of this particular technique, the obtained iron oxide particles are precipitated out of solution using ethanol. Here, however, the iron oxide particles are still impure on account of the particles being embedded within a range of unreacted organic compounds (oleic acid) and reaction solvents (1-octadecene) employed during the thermal decomposition reaction, as well as a number of by-products emerging from the reaction. Park et al[1] outlines a method in the literature to remove the excess oleic acid and 1-octadecene impurities by washing the impure iron oxide particles with copious amounts of ethanol. Yet, in practice, there is little evidence to suggest that the sole use of ethanol can remove all the impurities associated with this thermal decomposition reaction.

For biomedical and other consumer-based applications, the purification of the metal oxide particles is critical as impurities can influence a range of factors such a magnetic particle performance, size and subsequent phase transfer of these particles to aqueous or other polar solvents. For instance, if the surface of a particle is not sufficiently clean, a solution containing such impure particles will not behave like a colloidal suspension, causing the particles to aggregate, which may in turn affect their magnetic properties, and subsequently their application. Moreover, the large size due to particle aggregation will also affect their biological applicability, for instance their uptake mechanism by different organs, organelles and the lymphatic system.

Thus, there is an important need to remove excess reaction by-products from the surface of such metal oxide particles in a controllable and reproducible manner.

The present invention seeks to provide a method of purifying metal oxide particles post chemical synthesis, and uses thereof, which will overcome or substantially ameliorate at least some of the deficiencies of the prior art, or to at least provide an alternative.

SUMMARY OF THE INVENTION

According to a first aspect of the present invention, there is provided a method of purifying a plurality of metal oxide particles produced from a synthesis process, the method comprising the step of:

a) washing a plurality of metal oxide particles in a first solvent composition comprising of:

i) at least one aliphatic ether; and ii) at least one flocculant.

Preferably, the at least one aliphatic ether is at least partially miscible with the at least one flocculant.

Preferably, the at least one aliphatic ether and the at least one flocculant are in a 1:1 (vol/vol) ratio.

Preferably, the at least one aliphatic ether is selected from the group consisting of a primary aliphatic ether, a secondary aliphatic ether and a tertiary aliphatic ether.

Preferably, the at least one aliphatic ether is selected from the group consisting of diethyl ether, di-n-propyl ether, tert-butyl methyl ether and di-n-octyl ether.

Preferably, the at least one flocculant is selected from the group consisting of an alcohol, an aldehyde and a ketone.

Preferably, the at least one flocculant is an alcohol selected from the group consisting of a primary alcohol, a secondary alcohol and a tertiary alcohol.

Preferably, the alcohol is a primary alcohol selected from the group consisting of methanol, ethanol and n-propanol.

Preferably, the at least one aliphatic ether is diethyl ether and the at least one flocculant is methanol.

Preferably, the first solvent composition further comprises at least one non-polar solvent.

Preferably, the at least one aliphatic ether and the at least one non-polar solvent are at least partially miscible with the at least one flocculant.

Preferably, the at least one aliphatic ether, the at least one non-polar solvent and the at least one flocculant are in a 1:1:2 (vol/vol) ratio.

Preferably, the least one non-polar solvent is hexane.

Preferably, the method further comprises, after step a), the step of:
 b) further washing said plurality of washed metal oxide particles in a second solvent composition comprising of:
  i) at least one non-polar solvent; and
  ii) at least one flocculant.

Preferably, the at least one non-polar solvent is at least partially miscible with the at least one flocculant.

Preferably, the at least one non-polar solvent and the at least one flocculant are in a 1:1 (vol/vol) ratio.

Preferably, the at least one non-polar solvent is hexane and the at least one flocculant is ethanol.

Preferably, the method further comprises, after step a) but before step b), the step of:
 a1) separating the plurality of washed metal oxide particles from the first solvent composition using a physical separation procedure.

Preferably, the physical separation procedure is selected from the group consisting of magnetic separation, centrifugation, filtration and decantation.

Preferably, the method further comprises, after step b), the step of:
 c) dispersing said plurality of further washed metal oxide particles in a third solvent composition which is comprised of:
  i) at least one non-polar solvent.

Preferably, the least one non-polar solvent is hexane.

Preferably, the method further comprises, after step b) but before step c), the step of:
 b1) separating the plurality of further washed metal oxide particles from the second solvent composition using a physical separation procedure.

Preferably, the physical separation procedure is selected from the group consisting of magnetic separation, centrifugation, filtration and decantation.

According to a second aspect of the present invention, there is provided a method of purifying a plurality of iron oxide particles produced from a thermal decomposition synthesis process between an iron-oleate complex and oleic acid in 1-octadecene, the method comprising the steps of:
 a) washing a plurality of iron oxide particles in a first solvent composition comprising of diethyl ether and methanol in a 1:1 (vol/vol) ratio;
 b) further washing said plurality of washed iron oxide particles in a second solvent composition comprising of hexane and ethanol in a 1:1 (vol/vol) ratio; and
 c) dispersing said plurality of washed iron oxide particles in hexane.

Preferably, the method further comprises, after step a) but before step b), the step of:
 a1) separating the plurality of washed iron oxide particles from the first solvent composition using a physical separation procedure Preferably, the method further comprises, after step b) but before step c), the step of:
 b1) separating the plurality of further washed iron oxide particles from the second solvent composition using a physical separation procedure.

Preferably, the method further comprises, the step of:
 d) repeating one or more of steps a) to c).

According to a third aspect of the present invention, there is provided a use of iron oxide particles purified according to the method of the second aspect as a contrast agent for magnetic resonance imaging (MRI).

According to a fourth aspect of the present invention, there is provided a use of iron oxide particles purified according to the method of the second aspect as magnetic particles in a magnetism-assisted process selected from the group of processes consisting of magnetic separation, magnetism-directed targeting and magnetism-induced heating.

Other aspects of the invention are also disclosed.

BRIEF DESCRIPTION OF THE DRAWINGS

Notwithstanding any other forms which may fall within the scope of the present invention, preferred embodiments of the invention will now be described, by way of example only, with reference to the accompanying drawings in which.

DETAILED DESCRIPTION OF SPECIFIC EMBODIMENTS

Figure 1:
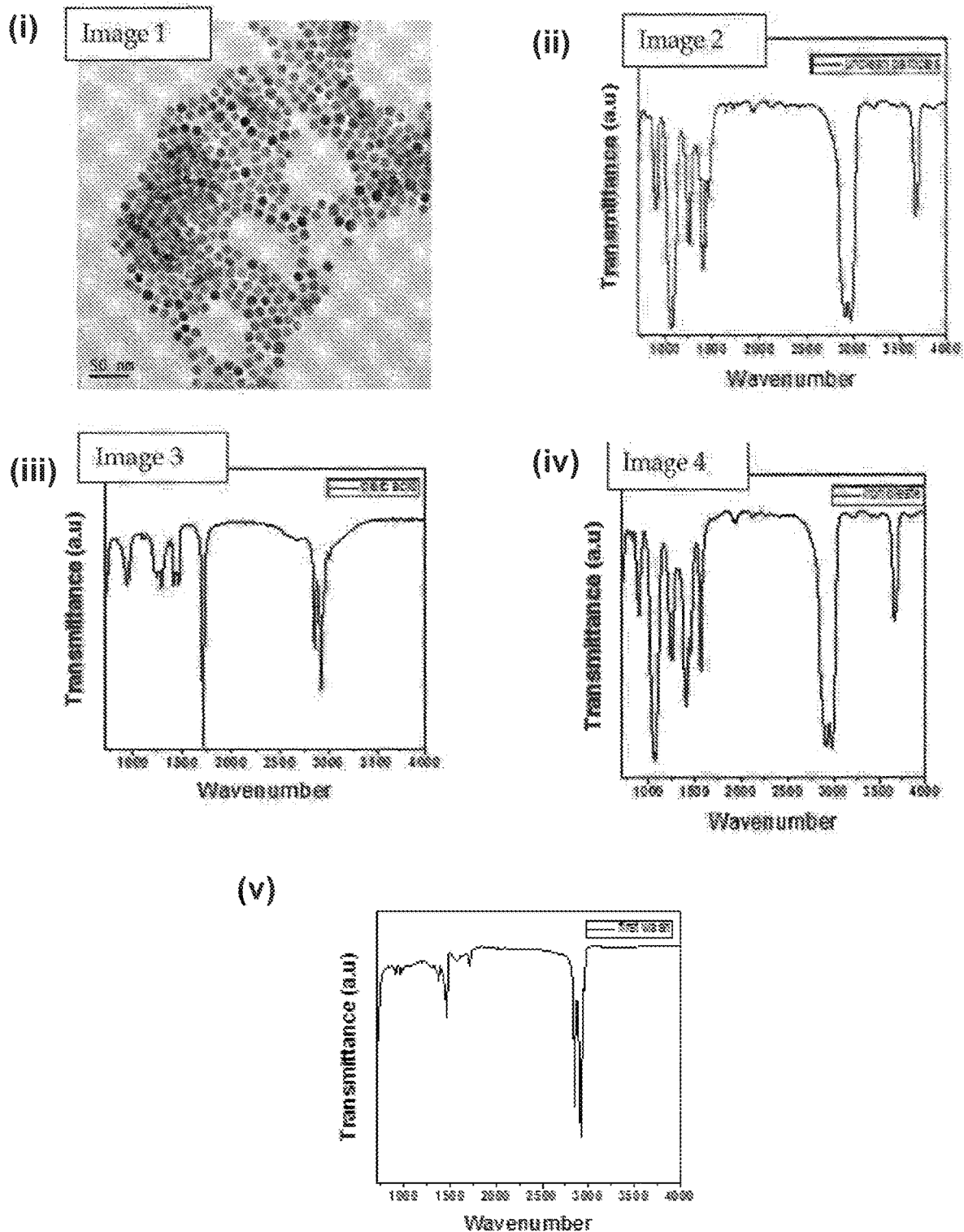
FIG. 1 shows (i) a TEM image of iron oxide particles purified using a method according to a preferred embodiment of the present invention involving a first solvent composition comprising a 1:1 ratio of non-polar solvent (diethyl ether) to flocculant (methanol) and a second solvent composition comprising a 1:1 ratio of non-polar solvent (hexane) to flocculant (ethanol), together with FTIR spectra of (ii) the iron oxide particles prior to cleaning, (iii) oleic acid, (iv) iron oleate, and (v) the iron oxide particles, post cleaning.

The present invention is predicated on the finding of a method for purifying metal oxide particles produced according to any one of a number of metal oxide particle synthesis processes including but not limited to thermal decomposition methods, hydrothermal synthesis methods, co-precipitation methods and micro-emulsion techniques. Regardless of the synthesis process, all metal oxide particle synthesis processes require a level of rigorous purification to remove the excess reactants and the associated by-products.

One of the most commonly used and preferred synthesis processes to produce iron oxide particles is the thermal decomposition method employed by Park et al[1], because of the desirable properties achieved using this method such as monodispersity and high crystallinity, as well as the propensity for large-scale manufacturing. In the last phase of the thermal decomposition method, iron oxide particles are precipitated out of the reaction solution using ethanol. The iron oxide particles obtained in this manner are typically embedded within a range of unreacted organic compounds and reaction solvents used during the synthesis, such as excess oleic acid and 1-octadecene. To address this, Park et al[1] relies on a purification step in which the precipitated iron oxide particles are washed in copious amounts of ethanol to remove the unwanted organic contaminants. However, in practice, there is little evidence that the sole use of ethanol is sufficient to remove these unwanted organic contaminants.

Embodiments of the present invention will be described in terms of purifying a plurality of iron oxide particles produced according to the thermal decomposition method employed by Park et al[1]. However, it will be appreciated by those skilled in the relevant art that the rigorous cleaning protocol outlined below could equally be employed in the purification of iron oxide particles, and indeed other metal oxide particles, produced according to one of the other highlighted syntheses processes Method A method of purifying a plurality of iron oxide particles produced from a thermal decomposition synthesis process between an iron-oleate complex and oleic acid in 1-octadecene according to a preferred embodiment of the present invention will now be described.

The method comprises, as a first step, step a), the step of washing the plurality of as-produced iron oxide particles in a first solvent composition comprising of an aliphatic ether and a flocculant in the form of a solvent.

The inventors have found that the choice of aliphatic ether and flocculant is dependent on the basis that these solvents should be at least partially miscible with each other.

The aliphatic ether may be a primary, secondary or tertiary aliphatic ether.

As will be described in the examples below, good results have been obtained when the aliphatic ether is selected from the group consisting of diethyl ether, di-n-propyl ether, tert-butyl methyl ether (TBME) and di-n-octyl ether.

In a preferred embodiment, the aliphatic ether is diethyl ether.

The flocculant may be selected from the group consisting of an alcohol, an aldehyde and a ketone.

Suitably, the flocculant is a low order alcohol selected from the group consisting of a primary alcohol, a secondary alcohol and a tertiary alcohol.

In one embodiment, the low order alcohol is a primary alcohol selected from the group consisting of methanol, ethanol and n-propanol.

In a preferred embodiment, the flocculant is methanol.

The inventors have found that the ratio of aliphatic ether to flocculant in the first solvent composition may be varied by up to 20% (for example, approximately a 5 ml variation of either solvent) and still achieve an effective cleaning protocol.

In a preferred embodiment, the aliphatic ether and the flocculant are in a 1:1 (vol/vol) ratio. Good results detailing the effectiveness of this 1:1 (vol/vol) ratio can be found in the Examples and Table provided below.

The inventors have also found that the ratio of solvent used in the first solvent composition to the amount of iron oxide particles is critical to achieving a good cleaning protocol. For instance, as shown in Table 1, the study as exemplified in Examples 5A to 5E described below, demonstrates that as the ratio of solvent to iron oxides particles transitions from 49.0:1.0 to 47.0:3.0, the effectiveness of the cleaning protocol steadily worsens.

Whilst not wishing to be bound by any one particular theory, the inventors believe that this reduced cleaning efficiency is due, at least in part, to finite miscibility of contaminant species bound onto as-prepared iron oxide particles with the solvent mixture used for cleaning, along with an equilibrium state responsible for co-existence of contaminant species bound onto particles surface and those in the solvent mixture.

As will be described in Example 1 below, excellent results have been obtained when the first solvent composition comprises diethyl ether and methanol in a 1:1 (vol/vol) ratio, where the ratio of solvent to iron oxide particles is 49:1.

The inventors have also found that the first solvent composition may further comprise a non-polar solvent, in addition to the aliphatic ether and the flocculant. It will be appreciated by those skilled in the relevant art that the choice of non-polar solvent, aliphatic ether and flocculant is dependent on the basis that these solvents should be at least partially miscible with each other.

In a preferred embodiment, the non-polar solvent is hexane.

As will be described in Example 19 below, good results have been obtained when the first solvent composition comprises hexane, diethyl ether and methanol in a 1:1:2 (vol/vol) ratio, where the ratio of solvent to iron oxide particles is 49:1.

Once washed, the plurality of washed iron oxide particles are then isolated from the first solvent composition using a physical separation procedure. It will be appreciated by those skilled in the relevant art that any one of a number of standard procedures may be used to isolate the washed iron oxide particles, including but not limited to, magnetic separation, centrifugation, filtration and decantation.

As will be described in the examples below, good results have been obtained when the plurality of washed iron oxide particles are separated from the first solvent composition using magnetic separation.

The method comprises, as a second step, step b), the step of further washing the plurality of iron oxide particles washed according to step a) in a second solvent composition comprising of a non-polar solvent and a flocculant.

Again, the inventors have found that the choice of non-polar solvent and flocculant is dependent on the basis that these solvents should be at least partially miscible with each other.

In a preferred embodiment, the non-polar solvent is hexane and the flocculant is ethanol used in a 1:1 (vol/vol) ratio.

Again, once washed, the plurality of further washed iron oxide particles are then isolated from the second solvent composition using a physical separation procedure such as magnetic separation.

The method comprises, as a third step, step c), the step of dispersing the plurality of further washed iron oxide particles in a third solvent composition which is comprised of a non-polar solvent.

In a preferred embodiment, the non-polar solvent is hexane.

It will be appreciated by those skilled in the relevant art that any one of steps a) to c) of the cleaning protocol described above may be repeated, according to step d), to achieve the desired purity.

In essence, the inventors have found that by conducting each of steps a) to c) of the cleaning protocol described above, it is possible to obtain iron oxide particles of sufficient purity to render them viable for a range of biomedical applications such as therapeutics, bio-sensing, cell separation and staining, magnetic separation techniques for separating a desired entity in solution from, for example, chemical reactants and/or by-products, magnetism-directed targeting, magnetism-induced heating, and as a contrast agent for magnetic resonance imaging (MRI).

The following examples and figures are provided for illustrative purposes. It is thus understood that the examples and figures are not to be construed as limiting. The skilled person in the art will clearly be able to envisage further modifications of the principles laid out herein.

EXAMPLES

Example 1

Impure iron oxide particles were obtained according to the thermal decomposition method as outlined in Park et al[1], albeit with some slight differences in that, an anhydrous iron (III) chloride precursor was used for the synthesis instead of iron (III) chloride hexahydrate, and the post-synthesis step of precipitating the obtained iron oxide particles from solution using copious amounts of ethanol was not employed.

Briefly, to 1 mL of the obtained iron oxide particles was added 49 mL of a first solvent composition comprising a (1:1 vol/vol) mixture of the non-polar solvent, diethyl ether, and the flocculent, methanol. The highly waxy iron oxide particles dispersed readily in the first solvent composition, and the majority of the particles immediately precipitated out of solution.

The mixture was then sonicated for 5 minutes to facilitate efficient cleaning of the iron oxide particles. The iron oxide particles were then magnetically separated from the solution by applying a magnet immediately to the outside of the reaction vessel for approximately 2 to 3 minutes. Magnetic separation of the iron oxide particles indicated purification, as prior to cleaning; the impure iron oxide particles obtained from the thermal decomposition process could not be magnetically separated from the surrounding organic solvents and impurities. The supernatant was decanted off while the now separated iron oxide particles remained at the bottom of the vessel on account of the external magnetic field. The magnet was then removed and then the semi-purified iron oxide particles were subjected to a second solvent composition comprising a non-polar solvent in the form of hexane and a flocculent in the form of ethanol. Here, the hexane (10 mL) was added first to cause the semi-purified iron oxide particles to redisperse into solution, turning the solution black. The ethanol (10 mL) was then added to the solution and the resulting mixture was sonicated for 5 minutes. The iron oxide particles were again magnetically separated according to the same procedure as described above. The cleaned iron oxide particles appeared black, wet and without an oily sheen or residue. Finally, the cleaned iron oxide particles were dispersed in hexane to form a colloidal suspension.

The efficiency of the cleaning protocol of Example 1 was assessed via transmission electron microscopy (TEM) and Fourier transform infrared spectroscopy (FTIR) of the obtained iron oxide particles dried under ambient conditions.

This example shows a rapid (5-15 minutes), low cost (~0.2 L versus tens of litres of organic solvents for purification), environmentally friendly (by minimising organic solvent wastes), high yield and more effective (i.e. better cleaning) method for the purification of iron oxide particles from residual solvents and organic impurities. Furthermore, the ability to magnetically separate the cleaned iron oxide particles throughout the purification process is further evidence of the excellent cleaning efficacy of this protocol.

As shown in FIG. 1(i), the TEM image of the iron oxide particles cleaned according to the aforementioned cleaning protocol demonstrates the effectiveness of this method. Indeed, the TEM image reveals iron oxide particles that are isolated and monodispersed, confirming that the excess reactants and by-products associated with the thermal decomposition synthesis have been completely removed from the surface of these iron oxide particles.

FTIR is a useful technique for assessing the nature and relative abundance of any organic impurity that might be present on the surface of the iron oxide particles obtained from the thermal decomposition synthesis, pre- and post-purification. This, in turn, will reflect upon the level of purification achieved through a particular cleaning protocol.

FIG. 1(v) shows an FTIR spectrum of the iron oxide particles following cleaning using the protocol of Example 1. The FTIR signatures in this spectrum are then compared with the signatures in the corresponding FTIR spectrum of the impure iron oxide particles prior to cleaning (FIG. 1(ii)), and those in the FTIR spectra of the chemical precursors used in the thermal decomposition synthesis, namely oleic acid (FIG. 1(iii)) and iron oleate (FIG. 1(iv)).

The FTIR spectrum shown in FIG. 1(ii) reveals that the impure iron oxide particles show a large number of peaks at different vibration frequencies, many of which overlap with the FTIR signatures associated with the chemical precursors employed during the thermal decomposition synthesis. This overlapping of peaks suggests that a large number of impurities remain bound to the surface of the impure iron oxide particles.

In contrast, when the impure iron oxide particles are cleaned by employing the above-described protocol, the cleaned iron oxide particles show only limited features, thereby suggesting in the first instance of most of the impurities have been removed during the cleaning process. Specifically, as is apparent from the FTIR spectrum in FIG. 1(v), the cleaned iron oxide particles show major vibrational features in the range 1200 $cm^{-1}$ to 1600 $cm^{-1}$ and 2800 $cm^{-1}$ to 3000 cm$^{-1}$. These features match well with those associated with native oleic acid (FIG. 1(iii)), but not with the iron oleate (FIG. 1(iv)), confirming that most of the iron oleate is removed during the cleaning process. Considering that iron oleate (a highly waxy semisolid) is extremely difficult to remove during standard cleaning or purification protocols, these observations affirms the high efficacy of the cleaning protocol described in Example 1.

Careful analysis of the FTIR vibrations observed in the spectrum (FIG. 1(v)) of the cleaned iron oxide particles further confirms that most of the iron oleate and free oleic acid have been removed during cleaning, while oleic acid molecules bind to the particle surface in a highly organised compact manner. For instance, the minor peaks at 1377 cm$^{-1}$ and 1463 cm$^{-1}$ in the FTIR spectrum of the cleaned iron oxide particles (FIG. 1(v)) correspond to the asymmetric and symmetric vibrations of metal carboxylates. The wavenumber separation ($\Delta_{vO}$) between $v_{as}(COO^-)$ and $v_s(COO^-)$ IR bands can be used to determine the interaction between the carboxylate and the metal ions. (Bronstein, 2007).[3] In the case of the cleaned iron oxide particles, the wavenumber separation ($\Delta_{vO}$) is 86 cm$^{-1}$, which is ascribed to a bidentate chelating coordination where the COO group forms a covalent bond with the iron atom. This result suggests that after cleaning, a small amount of iron oleate remained chemisorbed on the particle surface as carboxylate, thereby stabilising the particles against aggregation.

Another important peak observed in the FTIR spectrum (FIG. 1(v)) for the cleaned iron oxide particles occurs at 1716 cm$^{-1}$, which corresponds to the vibration associated with oleic acid. This peak is noticeably absent from the FTIR spectrum ((FIG. 1(iv)) for iron oleate. This peak arises from the stretching vibrations of the carboxyl group (C=O) of the oleic acid molecules. Notably, the intensity of this peak in the cleaned iron oxide particles is significantly lower than that in oleic acid. This supports the presence of a significantly reduced surface layer of oleic acid around the iron oleate capped oxide particles.

Additional peaks at 2850 cm$^{-1}$ and 2918 cm$^{-1}$ in the FTIR spectrum (FIG. 1(v)) of the cleaned iron oxide particles correspond to the symmetric and asymmetric stretching vibrations of the methylene (CH$_2$) bonds. The long chain carbon chains of both oleic acid and iron oleate contribute to these FTIR signatures, as is evidenced from the FTIR spectra of these pure precursors. However, the observed signatures in this vibrational range are significantly broader in the FTIR spectrum (FIG. 1(iv)) of the iron oleate and in the FTIR spectrum (FIG. 1(ii)) of the impure iron oxide particles as compared with those in the FTIR spectra for oleic acid (FIG. 1(iii)) and the cleaned iron oxide particles ((FIG. 1(v)). The sharpening of these features in the FTIR spectrum (FIG. 1(v)) for the cleaned iron oxide particles is indicative of a highly close packed crystalline structuring of the hydrocarbon chains in the monolayer surrounding the particles. This supports the above notion that after cleaning, iron oleate forms the first monolayer immediately around the clean iron oxide particles, followed by an additional oleic acid layer. In this assembly, significant hydrophobic interactions between the long carbon chains of iron oleate and oleic acid lead to tight packing of the methylene (CH$_2$) stretching vibrations.

In summary, therefore, the inventors have surprisingly found that the cleaning protocol of Example 1 removes most of the unreacted chemical precursors and by-products associated with the thermal decomposition synthesis in a simple washing step.

It will be appreciated that the flocculant, methanol, may be exchanged for ethanol, propanol or acetone.

Example 2—Twofold Wash with Second Solvent Composition

This present example follows a similar cleaning protocol to that described in Example 1, with the exception that the cleaning protocol described here comprises an additional step of washing the cleaned iron oxide particles a second time with the second solvent composition (1:1 ratio of hexane and ethanol).

As shown in FIG. 2(i), the TEM image of the purified iron oxide particles cleaned according to the protocol of Example 2 demonstrates that the additional cleaning step involving the second solvent composition does not seem to further influence the quality of the obtained iron oxide particles, where the particles remain monodispersed and well isolated.

Figure 2:
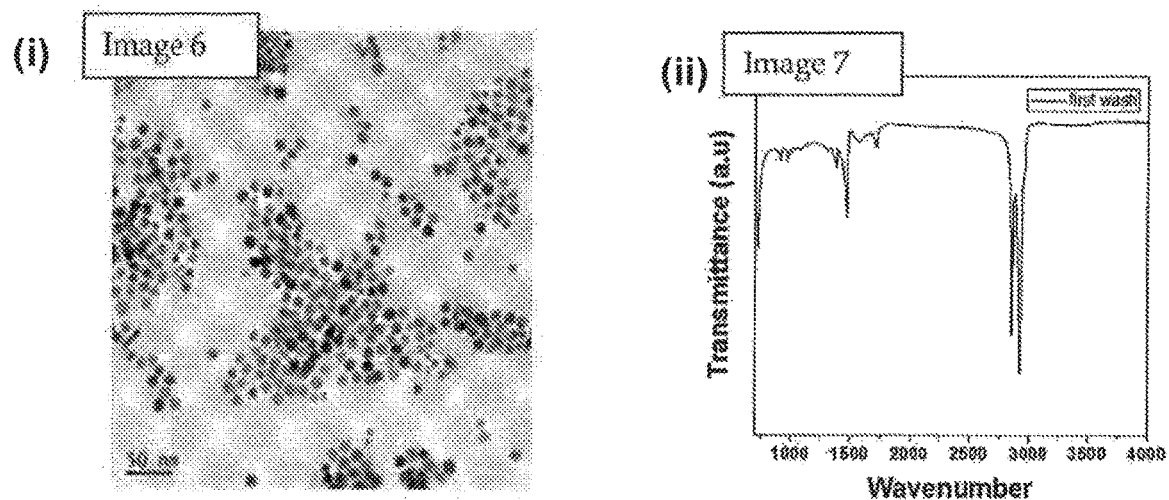
FIGS. 2 to 4 each show (i) a TEM image and (ii) an FTIR spectrum of the iron oxide particles purified according to the method of the preferred embodiment, with one or more additional washing step(s) using the second solvent composition.

The FTIR spectrum shown in FIG. 2(ii), however, indicates some changes in the organic molecules present on the surface of the cleaned iron oxide particles. The major changes are noted in the 1200 cm$^{-1}$ to 1600 cm$^{-1}$ vibrational range, such that the asymmetric and symmetric vibrations of the metal carboxylates were observed at 1375 and 1541 cm$^{-1}$, respectively. This shifts the ($\Delta_{vO}$) between the $v_{as}(COO^-)$ and $v_s(COO^-)$ IR bands from 86 cm$^{-1}$ (as observed in respect of the cleaning protocol of Example 1) to 166 cm$^{-1}$ in the protocol of Example 2.

Whilst not wishing to be bound by any one particular theory, the inventors are of the view that this change in value strongly suggests that the nature of coordination of the COO$^-$ group to the metal ion changes from bidentate chelating to a predominantly bridging ligand configuration. As such, this indicates a change in the nature of the bonding between the iron oxide particles and the oleate species from covalent towards ionic and hydrogen bonding. Considering that the strength of covalent bonds is significantly higher than those of other bonds, the additional cleaning step involving the second solvent composition (1:1 ratio of hexane to ethanol) appears to loosen the layer of organic molecules bound to the surface of the iron oxide particles.

Example 3—Fourfold Wash with Second Solvent Composition

This present example follows a similar particle cleaning protocol as described in Example 1, with the exception that in the cleaning protocol described here, the step of washing the cleaned iron oxide particles using the second solvent composition (1:1 ratio of hexane and ethanol) is repeated a further three (3) times.

As shown in FIG. 3(i), the TEM image of the purified iron oxide particles cleaned according to the protocol of Example 3 demonstrates that the additional washing steps involving the second solvent composition does not seem to further influence the quality of the cleaned iron oxide particles, such that the particles remain monodispersed and well isolated.

Figure 3:
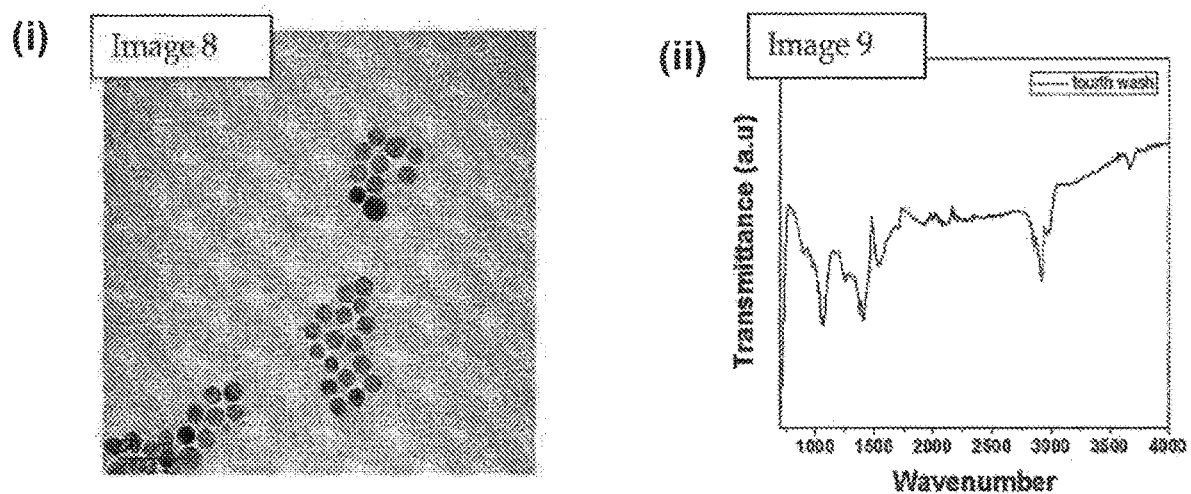

However, as in the case of Example 2, the FTIR spectrum (FIG. 3(ii)) of the purified iron oxide particles cleaned according to the protocol of Example 3 clearly indicates significant changes in the organic molecules present on the surface of the cleaned iron oxide particles. For instance, in the 1200 cm$^{-1}$ to 1600 cm$^{-1}$ vibrational range, the asymmetric and symmetric vibrations of metal carboxylates were observed at 1405 cm$^{-1}$ and 1532 cm$^{-1}$, respectively, which corresponds to the wavenumber separation ($\Delta_{vO}$) of 127 cm$^{-1}$, signifying that the nature of coordination of the COO to the metal ion remains predominantly in a bridging ligand configuration, as in the case of Example 2. This configuration corresponds to less tightly bound oleate species on the surface of the cleaned iron oxide particles.

A number of other changes in the FTIR spectrum (FIG. 3(ii)) for the cleaned iron oxide particles were observed, where the peaks look more similar to the peaks shown in the FTIR spectrum (FIG. 1(iv)) of iron oleate than that of oleic acid (FIG. 1(ii)).

For instance, new peaks at 1066 cm$^{-1}$ and 3675 cm$^{-1}$ observed in the FTIR spectrum (FIG. 3(iii)) for the cleaned iron oxide particles were not present in the FTIR spectrum of the iron oxide particles cleaned according to the protocols of Example 1 (FIG. 1(v)) and Example 2 (FIG. 2(ii)). Similarly, a broadening of the peaks in the 2800 cm$^{-1}$ to 3000 cm$^{-1}$ range observed in FIG. 3(ii) is similar to that observed in the FTIR spectrum (FIG. 1(iv)) for iron oleate, but dissimilar to that observed in the FTIR spectrum (FIG. 1(iii)) for oleic acid. The broadening of these peaks corresponding to the methylene (CH$_2$) vibrations is suggestive of a loosening of hydrophobic interactions between the alkyl chains. This is because most surface-bound oleic acid is removed as the number of washing steps is increased during the cleaning protocol, as discussed here in Example 3.

In summary, the FTIR analyses clearly reveal that after multiple cleaning steps according to the protocol of Example 3, a layer of oleate molecules becomes the predominant capping agent on the surface of the iron oxide particles.

Example 4—Sixfold Wash with Second Solvent Composition

This present example follows a similar particle cleaning protocol as described in Example 1, with the exception that in the cleaning protocol described here, the step of washing the cleaned iron oxide particles using the second solvent composition (1:1 ratio of hexane and ethanol) is repeated a further five (5) times.

As shown in FIG. 4(i), the TEM image of the purified iron oxide particles cleaned according to the protocol of Example 4 demonstrates that the additional five cleaning cycles involving the second solvent composition of hexane/ethanol do not seem to further influence the quality of the iron oxide particles, such that the particles remain monodispersed and well isolated during imaging.

Figure 4:
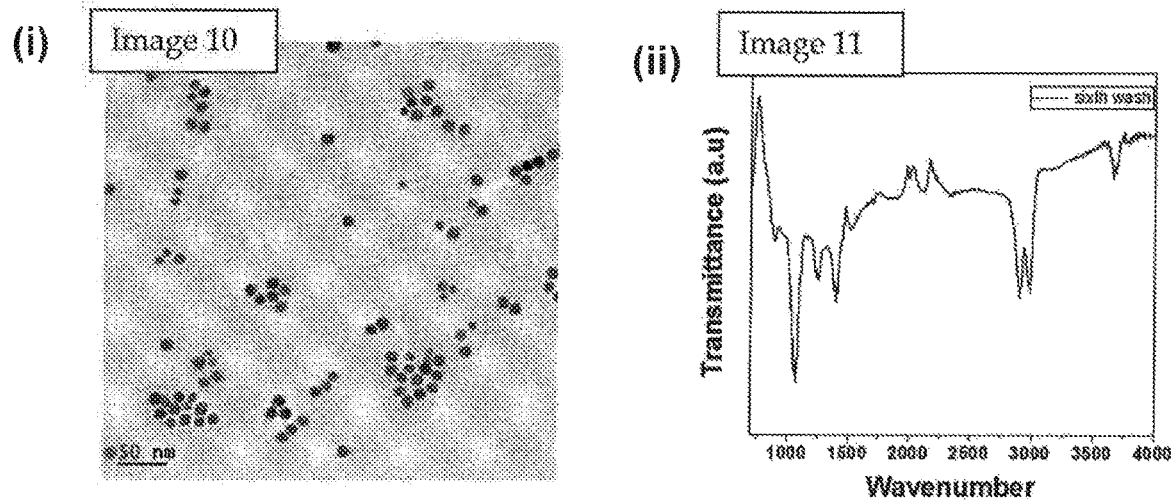

Similarly, the FTIR spectrum (FIG. 4(ii)) of the cleaned iron oxide particles clearly shows that the observed peaks in this spectrum correspond to those of the iron oxide particles obtained according to the protocol of Example 3 (FIG. 3(II)), albeit significantly more pronounced.

Whilst not wishing to be bound by any one particular theory, the inventors are of the view that only a very fine layer of oleate caps the surface of the iron oxide particles cleaned according to the protocol of Example 4. This impact upon the applicability of these particles, such that once these iron oxide particles are precipitated out of solution, it becomes extremely difficult to redisperse these particles in either a non-polar or polar solvent.

In summary, therefore, the inventors have found that the iron oxide particles purified according to the protocols described in Examples 1 and 2 are more readily redispersed in non-polar or polar solvents.

Examples 5A-5E—Varying First Solvent Composition to Iron Oxide Particle Ratio

This present example follows a similar particle cleaning protocol as described in Example 1, with the exception that the ratio of first solvent composition (1:1 diethyl ether to methanol) to the iron oxide particles to be purified was gradually decreased from the 49:1 ratio employed in the protocol of Example 1 to: 48.75:1.25 (Example 5A), 48.5:1.5 (Example 5B), 48.25:1.75 (Example 5C), 48.0:2.0 (Example 5D), and 47.0:3.0 (Example 5E). This was done to assess the impact of increasing the amount of impure iron oxide particles relative to the volume of the first solvent composition used in the cleaning protocol.

Figure 5A:
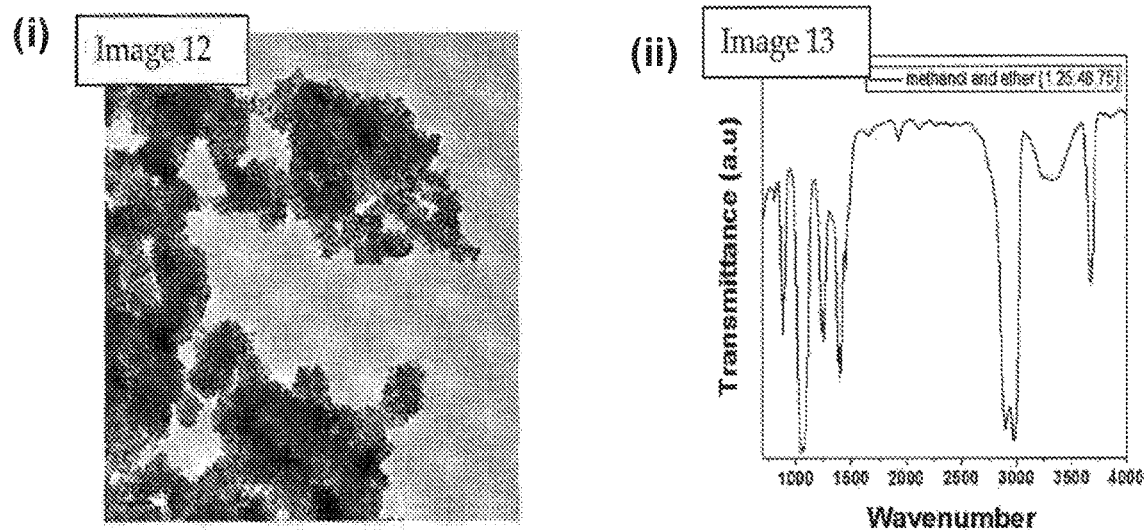
FIGS. 5A to 5E each show (i) a TEM image and (ii) an FTIR spectrum of the iron oxide particles purified according to the method of the preferred embodiment, in which the ratio between the first solvent composition and the metal oxide particles is varied.
Figure 5B:
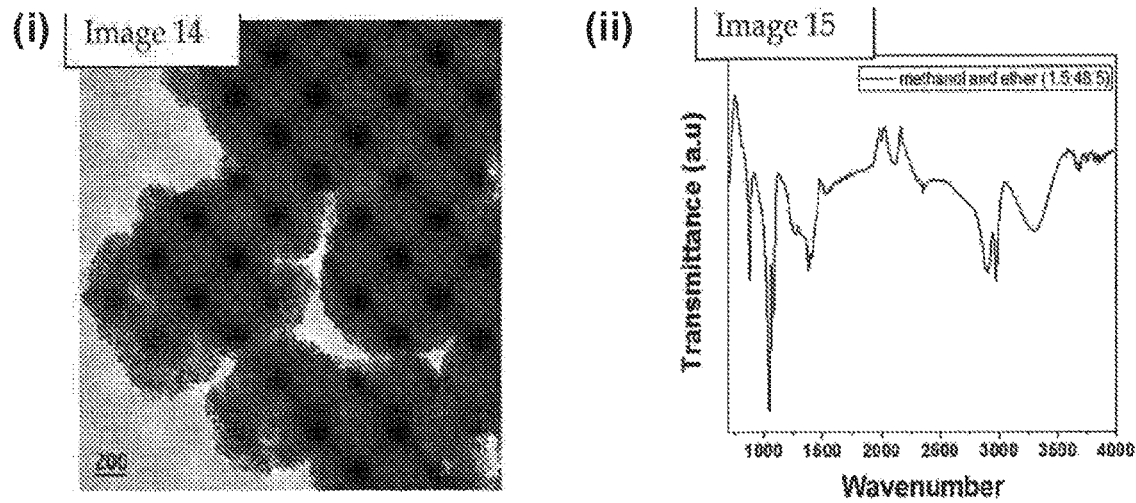
Figure 5C:
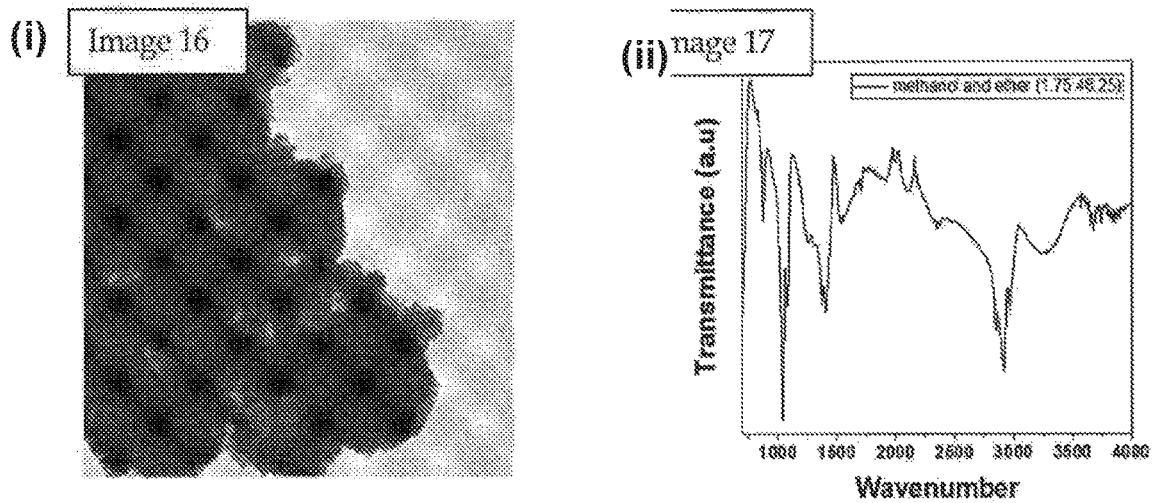
Figure 5D:
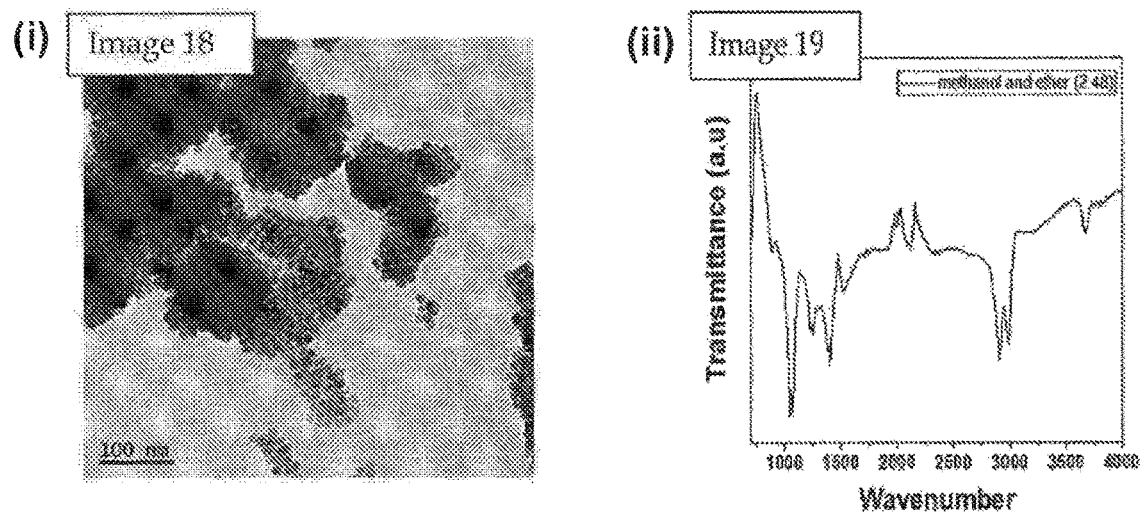
Figure 5E:
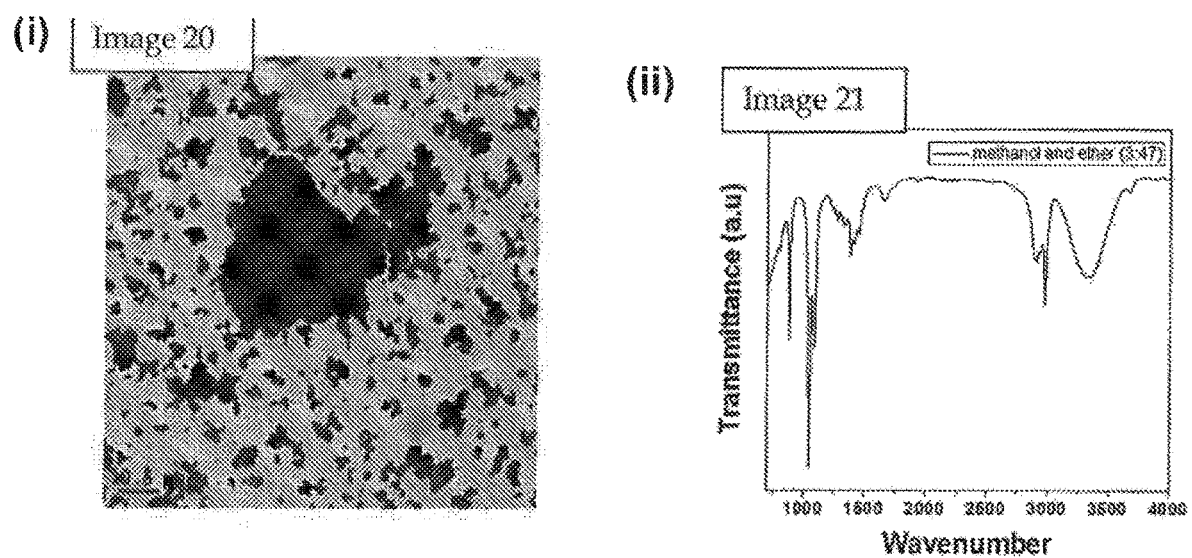

It is evident from the TEM images (FIG. 5A(i), FIG. 5B(i), FIG. 5C(i), FIG. 5D(i) and FIG. 5E(i)) for the iron oxide particles cleaned according to the protocols of Examples 5A to 5B, that by continuously decreasing the solvent to particle ratio, the cleaning efficiency is severely compromised, such that the cleaned iron oxide particles are poorly separated, and an oily layer is seen around the particle aggregates. In fact, the quality of the cleaned iron oxide particles becomes increasingly worse as the amount of first solvent composition is reduced.

Also, while the iron oxide particles cleaned according to the protocol of each of Examples 5A to 5E could be separated using an external magnet applied to the wall of the reaction vessel (suggesting some degree of cleaning), the process was not particularly efficient as it took longer to separate the iron oxide particles (suggesting inefficient cleaning) than it did for the iron oxide particles cleaned according to the protocol of Example 1. The iron oxide particles thus obtained using magnetic separation displayed a mild to strong oily sheen suggestive of a less than efficient cleaning protocol, in contrast to that seen for Example 1 above.

The FTIR spectra (FIG. 5A(ii), FIG. 5B(ii), FIG. 5C(ii), FIG. 5D(ii) and FIG. 5E(ii)) for the iron oxide particles cleaned according to the protocols of Examples 5A to 5B, clearly reveal that the semi-cleaned iron oxide particles obtained at each of these different solvent to particle ratios are similar to the impure iron oxide particles (FIG. 1(ii)) prior to any cleaning.

In summary, therefore, the inventors have found that an appropriate solvent to particle ratio is critical for an efficient cleaning methodology.

Example 6—Effect of Carbon Chain Length of the Non-Polar Solvent in the First Solvent Composition on Cleaning Efficiency This present example follows a similar cleaning protocol as described in Example 1, with the exception that the non-polar solvent (diethyl ether) used in the first solvent composition was substituted for di-n-propyl ether. This was done to assess the impact of the increasing carbon chain length of ethers on the cleaning efficiency in respect of the first solvent composition.

The inventors have found that while the iron oxide particles could not be purified to the same degree as when diethyl ether was used in the first solvent composition (Example 1), the iron oxide particles were still capable of being magnetically separated after the first washing step, thus indicating some degree of cleaning.

Indeed, it is evident from the TEM image (FIG. 6(i)) of the iron oxide particles cleaned according to the protocol of Example 6 that the iron oxide particles are only partially cleaned. Here, it was observed that most of the iron oxide particles were in the form of large aggregates with only a few iron oxide particles appearing as independent particles.

This may mean that if di-n-propyl ether is employed in the first solvent composition for cleaning, additional cleaning steps may be required.

Figure 6:
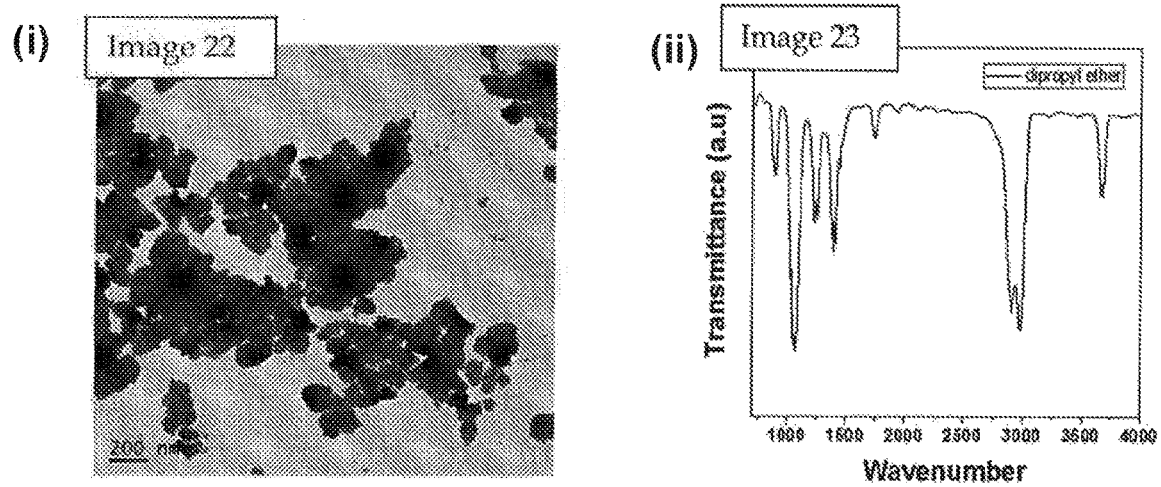
FIGS. 6 and 7 each show (i) a TEM image and (ii) an FTIR spectrum of iron oxide particles purified according to the method of the preferred embodiment, in which the non-polar solvent in the first solvent composition is substituted for di-n-propyl ether (FIG. 6) or tert-butyl methyl ether (FIG. 7)

As shown in FIG. 6(ii), the FTIR spectrum of these partially cleaned iron oxide particles is very similar to that observed for the iron oxide particles prior to cleaning (FIG. 1(ii)), but very different from that observed for the iron oxide particles cleaned according to the protocol of Example 1 (FIG. 1(v)).

In summary, the inventors have found that the choice of solvent for use in at least the first solvent composition is important for realising an efficient cleaning methodology.

Example 7—Substituting Diethyl Ether in the First Solvent Composition for Dioctyl Ether This present example employs a cleaning protocol similar to that described in Example 1, with the exception that the first solvent composition comprised the non-polar solvent, dioctyl ether as opposed to diethyl ether. This increase in the carbon chain length from C2 (ethyl) to C8 (octyl) corresponds to an increase in non-polarity of the solvent. In this respect, the similarity in the symmetric structures of diethyl ether and dioctyl ether could potentially allow the impact of non-polarity of the ether side groups on the cleaning efficiency of the iron oxide particles to be assessed.

However, the inventors found that the degree of non-polarity of the dioctyl ether rendered it immiscible with the other component of the first solvent composition, that being the methanol flocculant. As a result, the impure iron oxide particles added to this immiscible solvent mixture dispersed only in the dioctyl ether phase without interaction with the methanol phase. This proved problematic during the iron oxide particle cleaning procedure of Example 7 as without the direct availability of a suitable flocculant (i.e. methanol), the iron oxide particles could not be precipitated. Hence, further purification steps could not be performed and the iron oxide particles could not be purified using this first solvent composition.

Example 8—Substituting Diethyl Ether in the First Solvent Composition for Diphenyl Ether This present example follows a similar cleaning protocol as described in Example 1, with the exception that the first solvent composition comprised the non-polar solvent, diphenyl ether as opposed to diethyl ether. While diethyl ether has two aliphatic ethyl groups on either side of the oxygen molecule, the side groups of diphenyl ether are aromatic groups. In this respect, the similarity in the symmetric structures of diethyl ether and diphenyl ether could potentially allow the impact of non-polarity of either side chains on the particle cleaning protocol to be assessed.

Here, however, like in Example 7, the inventors found that the diphenyl ether and methanol components of the first solvent composition were immiscible. Thus, when the impure iron oxide particles were added to this immiscible solvent mixture, the iron oxide particles dispersed only in the diphenyl ether phase without interaction with the methanol phase. This again proved problematic during the particle cleaning protocol of Example 8 as without the direct availability of a suitable flocculant (i.e. methanol), the iron oxide particles could not be precipitated. Hence, further purification steps could not be performed and the iron oxide particles could not be purified using this first solvent composition.

Example 9—Substituting Diethyl Ether in the First Solvent Composition for Tert-Butyl Ethyl Ether (TBME)

This present example follows a similar cleaning protocol to that described in Example 1, with the exception that the first solvent composition comprised the non-polar solvent, tert-butyl ethyl ether (TBME) as opposed to diethyl ether. This was done to assess the impact of the position of the ether group and the symmetric nature of the ethers on cleaning efficiency. TBME was selected as it is an asymmetrical ether with the chemical structure, $(CH_3)_3COCH_3$. This significant change in structure was used to determine any impact on the purification process using R≠R', whilst maintaining its characteristic functional group.

Figure 7:
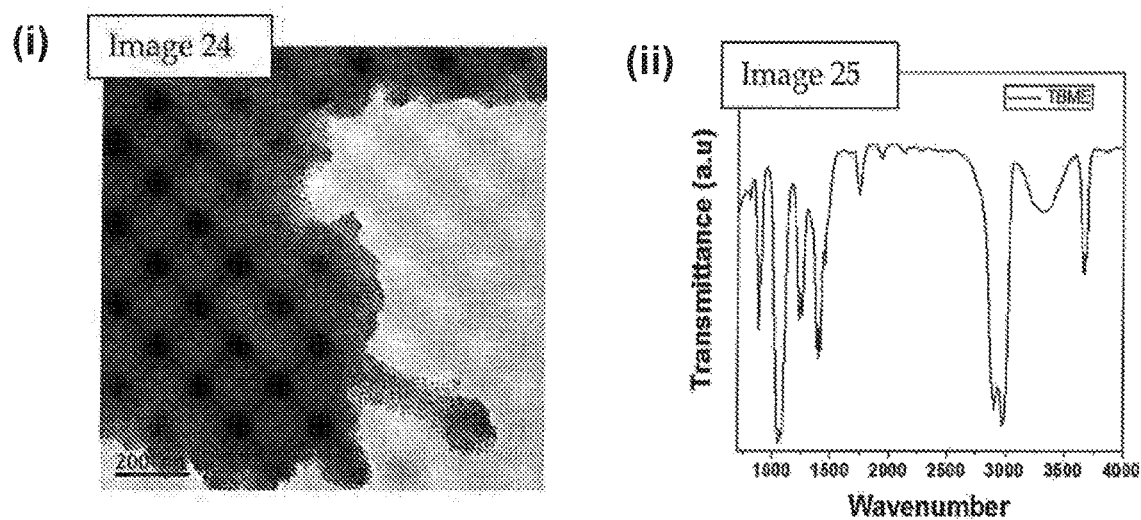

It is evident from the TEM image (FIG. 7(i)) and the FTIR spectrum (FIG. 7(ii)) for the iron oxide particles cleaned according to the protocol of Example 9 that by changing the non-polar solvent in the first solvent composition from diethyl ether to TBME, the impure particles could be partially cleaned, albeit not with the same efficiency as observed with diethyl ethyl (Example 1).

In summary, therefore, the inventors have found that the choice of an appropriate solvent is important for realising an efficient cleaning methodology.

Example 10—Substituting the Methanol Flocculant in the First Solvent Composition for Butanol The cleaning protocol of the present example is similar to that of Example 1, with the exception that the low order alcohol (such as methanol ethanol or propanol) used as a flocculant in the first solvent composition was replaced by a higher order alcohol (such as butanol) in the present example. This was done to assess if the use of a low order alcohol was critical for the purification process.

The inventors found, however, that butanol was not miscible with diethyl ether, which meant that the impure iron oxide particles remained in the top diethyl ether phase whilst the lower butanol layer remained clear. Followed by vigorous sonication, these particles were independently subjected to centrifugation and magnetic separation. However, the iron oxide particles obtained could not be separated by either of these techniques.

In summary, the inventors have found that at least partial miscibility of the non-polar solvent and flocculent in the first solvent composition is paramount to achieving a high cleaning efficiency of iron oxide particles, as demonstrated in Example 1.

Example 11—First Solvent Composition Comprising Only of Diethyl Ether

According to this example, the flocculant, methanol, was removed from the first solvent composition to determine if the use of methanol or another low-order alcohol as flocculant was critical for the purification process.

According to this protocol, diethyl ether (49 mL) was combined with 1 mL of the impure iron oxide particles and the resulting mixture was sonicated for 10 minutes. The iron oxide particles were then subjected to centrifugation and magnetic separation. However, the iron oxide particles could not be separated by either of these techniques.

In summary, the inventors have found that the inclusion of a lower order alcohol and/or a flocculant in the first solvent composition is critical for achieving purification of the iron oxide particles to the same level of purity as demonstrated in the cleaning protocol of Example 1.

Example 12—Comparative Example Based on the Cleaning Protocol Employed by Park Et Al[1]

This comparative example follows the iron oxide particle cleaning protocol described in Park et al.[1] in which the iron oxide particles were cleaned via repeated washing steps using an excess amount of a low order alcohol, which in the case of Park et al.[1] was ethanol.

To achieve this, 100 μL of impure iron oxide particles was added to 50 mL of ethanol in a 50 mL centrifuge tube and then mixed via sonication for two hours. The particle solution appeared to be immiscible with the ethanol even after extended periods of sonication. The particles were then collected by centrifugation and the supernatant was discarded. After centrifugation, the iron oxide particles were stuck to the inside wall of the centrifuge tube. 50 mL of additional ethanol was then added and the solution was sonicated for a further two hours in an attempt to dislodge the iron oxide particles from the inside wall of the centrifuge tube, and thus suspend them in the ethanol. This process was repeated 10 times over a number of days.

Here, however, the inventors found that despite extended sonication of the solution at each stage of the washing process, a number of the iron oxide particles could not be recovered after each washing step. Notably, it was not possible to magnetically separate the iron oxide particles until after the 4$^{th}$ ethanol wash, at which point less than half the sample could be magnetically separated, suggesting only a minor degree of cleaning at this stage.

The inventors observed that the amount of iron oxide particles capable of being magnetically separated increased gradually as the number of ethanol washes increased. However, it is widely apparent that a significant proportion of the iron oxide particles (over 50%) were lost during the cleaning steps.

Figure 8:
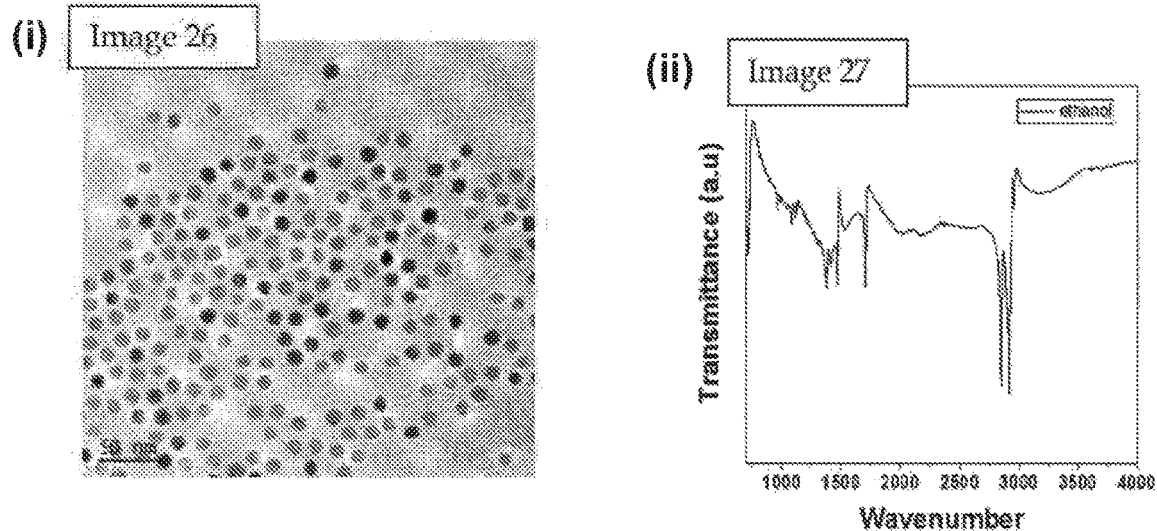
FIG. 8 shows, for comparison, (i) a TEM image and (ii) an FTIR spectrum of iron oxide particles purified using a method in which the first and second solvent compositions comprise only of a flocculant (ethanol)

It is evident from the TEM image (FIG. 8($i$)) of the iron oxide particles obtained that by employing ethanol in the cleaning protocol of Example 12, it was possible to obtain iron oxide particles with a reasonable degree of monodispersity and no obvious signs of impurities.

However, from a comparison of the FTIR spectrum (FIG. 8($ii$)) for the ethanol purified iron oxide particles obtained according to the cleaning protocol of Example 12 with the FTIR spectra for the impure iron oxide particles (FIG. 1($ii$)) and that (FIG. 1($v$)) of the iron oxide particles obtained according to the cleaning protocol of Example 1, it is clear that while washing with ethanol may clean the iron oxide particles to some extent, these particles are not as clean as those cleaned according to the protocol of Example 1.

In summary, the inventors have found that even though the use of ethanol as a solvent may result in a reasonable cleaning efficacy, there are not only significant drawbacks associated with this approach including time, labour, cost, and solvent-intensiveness, but also a significant loss of product during the cleaning process.

Example 13—Comparative Example Based on the Cleaning Protocol Employed by Burdinski, 2013)[2]

This comparative example follows an iron oxide cleaning protocol frequently cited in the prior art (Burdinski, 2013)[2] in which the first solvent composition comprises the non-polar solvent, hexane, in combination with a semi miscible or fully miscible polar solvent, most commonly ethanol, propanol, or acetone.

This cleaning protocol was investigated to compare the efficacy and effectiveness of this approach with the methodology employed in Example 1.

As a representative flocculant, acetone was combined with hexane at a (1:1 vol/vol) ratio. Impure iron oxide particles were then added to this solvent mixture at a (1:49 vol/vol) ratio and the mixture was sonicated for 5 minutes.

The inventors found that the iron oxide particles cleaned according to this approach could not be magnetically separated from the solution, and hence, they were instead collected by centrifugation at 10,000 RPM for 10 minutes. The obtained iron oxide particles were then suspended in 10 mL of hexane and 10 mL of ethanol was added. The resulting solution was then mixed for 10 minutes, sonicated for 5 minutes, and then the iron oxide particles were magnetically separated.

Figure 9:
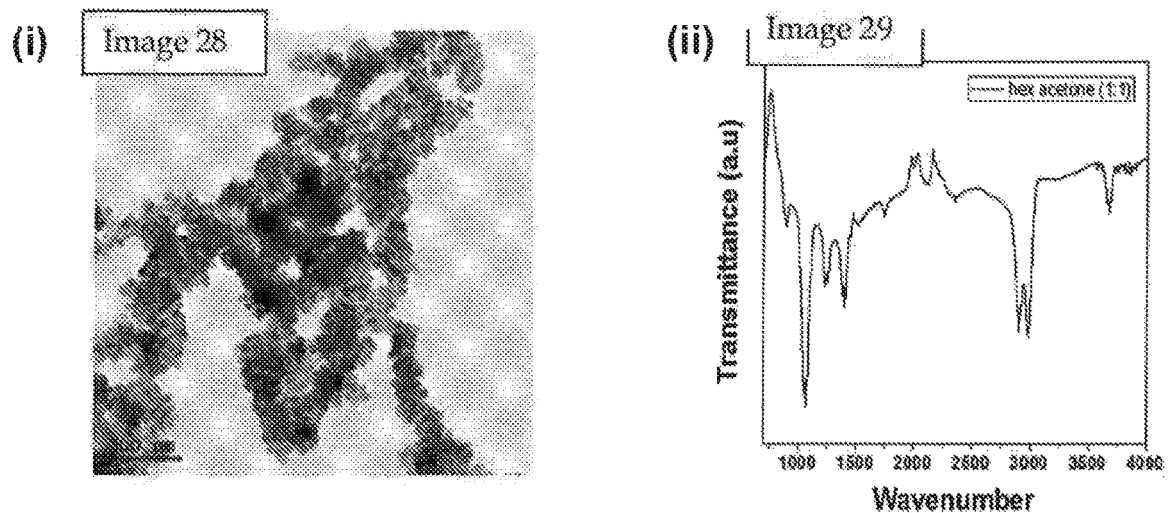
FIG. 9 shows (i) a TEM image and (ii) an FTIR spectrum of iron oxide particles purified according to the method of the preferred embodiment, in which the non-polar solvent and the flocculant in the first solvent composition are substituted for a 1:1 ratio of hexane and acetone, respectively.

As shown in the TEM image (FIG. 9($i$)) of the iron oxide particles obtained using this cleaning process, it is evident that the iron oxide particles could only be cleaned to a limited extent using a first solvent composition comprising hexane and acetone. Indeed, many of the iron oxide particles remained aggregated in small clumps.

Indeed, a comparison of the FTIR spectrum (FIG. 9($ii$)) of these semi cleaned iron oxide with the FTIR spectrum (FIG. 1($ii$)) for the impure iron oxide particles prior to cleaning, reveals a number of similarities, and is clearly therefore, very different to the FTIR spectrum (FIG. 1($v$)) obtained for the iron oxide particles cleaned according to the protocol of Example 1.

In summary, therefore, the inventors have found that while a first solvent composition comprising hexane and acetone provides a modest degree of cleaning, the iron oxide particles thus obtained are not as clean as those obtained according to the cleaning protocol of Example 1.

Example 14—Comparative Example Based on the Cleaning Protocol in Example 13 with a Twofold Increase in Flocculant Increasing the amount of flocculant(s) in the solvent composition has been reported to improve the precipitation and purification of particles (Burdinski, 2013)[2].

The present example is similar to the cleaning protocol of Example 13, albeit with the difference that the amount of flocculent (acetone or ethanol) used in the first solvent composition is twice that of hexane used in Example 13. Here, 1 mL of the impure iron oxide particles was heated at 50° C. and 10 mL of hexane, also heated to 50° C., was added to the heated iron oxide particles to obtain a homogenous solution. To this was added 20 mL of acetone to precipitate the iron oxide particles. The precipitated particles were subsequently collected by centrifugation at 5000 rpm for 30 minutes and resuspended in 5 mL of hexane, followed by addition of 10 mL of acetone. The particles were collected again by centrifugation and the washing process was repeated two more times.

Figure 10:
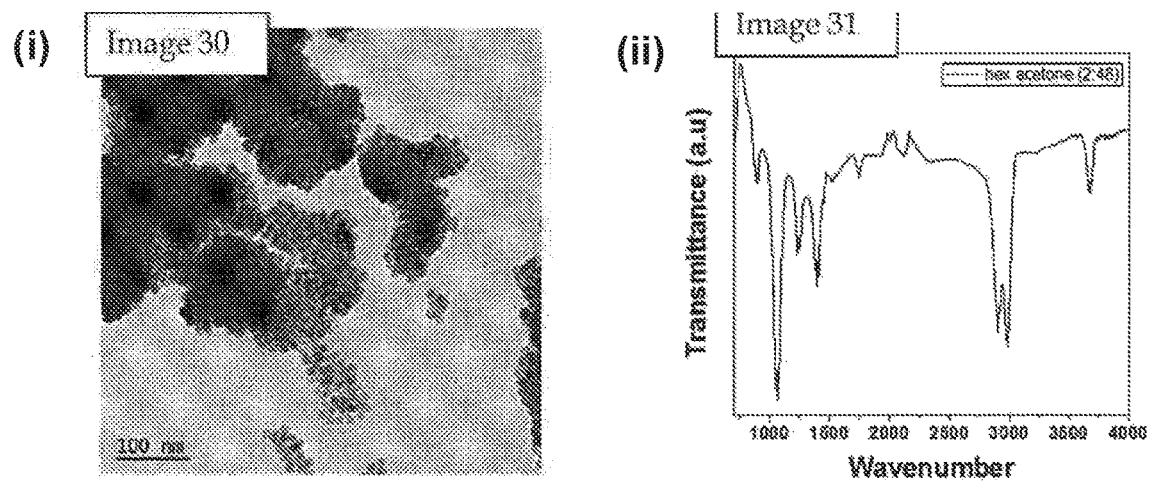
FIG. 10 shows (i) a TEM image and (ii) an FTIR spectrum of iron oxide particles purified according to the method of FIG. 9, in which each of the first and second solvent compositions comprise a 1:2 ratio of hexane to acetone.

As shown in FIG. 10($i$), the TEM image of the iron oxide particles cleaned according to the protocol of Example 14 reveals that increasing the amount of flocculant did not improve the quality and/or monodispersity of the iron oxide particles over those obtained by the protocol described in Example 13.

The FTIR spectrum (FIG. 10($ii$)) of the semi cleaned iron oxide particles shares a close resemblance to the corresponding FTIR spectrum of the impure iron oxide particles prior to cleaning (FIG. 1(ii)) and is very different from that observed for the cleaned iron oxide particles obtained according to the cleaning protocol of Example 1 (FIG. 1(v)).

Example 15—Comparative Example Substituting Diethyl Ether in the First Solvent Composition for Hexane According to this example, the first solvent composition comprised a combination of the non-polar solvent, hexane, and a low order alcohol in the form of either methanol or butanol as a flocculant, both of which remain immiscible with hexane.

When impure iron oxide particles were added to the first solvent composition, the inventors found that even after forced mixing through sonication, the impure iron oxide particles remained in the upper solvent layer of hexane whilst the bottom methanol or butanol layer remained completely clear. Moreover, all attempts to collect the iron oxide particles via centrifugation at 10,000 rpm for 30 minutes failed, where all of the iron oxide particles remained in solution and could not be precipitated.

Example 16—First Solvent Composition Comprising Only Non-Polar Solvents, Diethyl Ether and Hexane According to this example, the first solvent composition comprised a (1:1) combination of hexane and diethyl ether. The cleaning protocol was carried out by adding 49 mL of the first solvent composition to 1 mL of impure iron oxide particles. The mixture was sonicated for 10 minutes and the particles were then subjected to centrifugation at 10,000 rpm for 30 minutes. However, the particles could not be precipitated by centrifugation. Moreover, these particles could not be separated by magnetic separation. In a further step, 49 mL of ethanol was then added to this mixture as a flocculant to promote precipitation of the iron oxide particles. However, it was still not possible to collect the particles by centrifugation.

Example 17—First Solvent Composition Comprising Only Petrol

The suitability of petrol as a particle cleaning agent was assessed based on its non-polar nature and complex composition. According to this example, unleaded petrol containing n-hexane to n-nonane (12%), isomeric alkanes and n-butane (11%), cyclohexane and derivatives (5%), butene to hexene (25%), 1-nonene (12%), toluene (1%), xylenes (22%) and higher aromatics (11%) in approximate concentrations was used. This example is similar to Example 1, with the exception that the first cleaning step involved petrol instead of a solvent composition containing diethyl ether and methanol. Here, 49 mL of petrol was combined with 1 mL of impure iron oxide particles. This solution was mixed by sonication for 10 minutes. Following this primary washing step, a portion of the particles were capable of being magnetically separated, suggesting that petrol has some efficacy when cleaning iron oxide particles. However, to collect the total amount of iron oxide particles, centrifugation was performed at 5000 rpm for 30 minutes. The obtained iron oxide particles were resuspended in 20 mL of a second solvent composition comprising a (1:1 vol/vol) ratio of hexane and ethanol. This mixture was then sonicated for 10 minutes, followed by collection of the iron oxide particles via magnetic separation.

As shown in FIG. 11(i), the TEM image of the iron oxide particles cleaned according to the protocol of Example 17 reveals that while the iron oxide particles are cleaned to some extent, they remain embedded in organic material, thereby appearing as aggregates.

Figure 11:
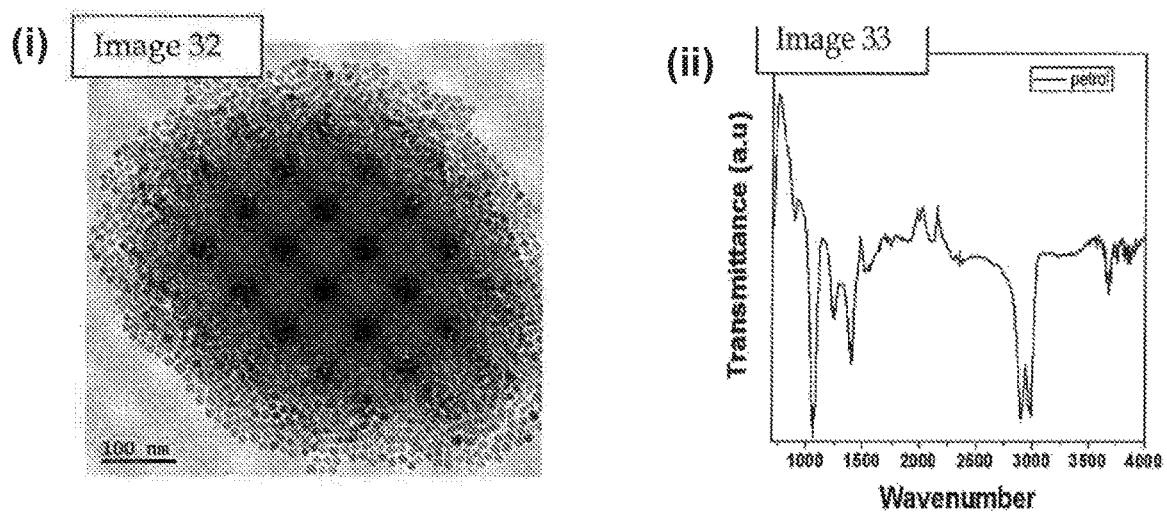
FIG. 11 shows, for comparison, (i) a TEM image and (ii) an FTIR spectrum of iron oxide particles purified using a method involving a first solvent composition comprising only a non-polar solvent (petrol) and a second solvent composition comprising a 1:1 ratio of non-polar solvent (hexane) to flocculant (ethanol)

The FTIR spectrum (FIG. 11(ii)) of these semi-cleaned iron oxide particles reveals less intense FTIR signatures than those observed in the FTIR spectrum (FIG. 1(ii)) for the impure iron oxide particles prior to cleaning, suggesting some degree of cleaning, but these signatures are significantly more prominent than those in the FTIR spectrum (FIG. 1(v)) of the iron oxide particles purified according to the cleaning protocol of Example 1.

Example 18—First Solvent Composition Comprising Petrol and Methanol

This present example is similar to the cleaning protocol described in Example 1, with the exception that petrol and methanol (1:1) were employed in the first solvent composition. After cleaning, it was found that the iron oxide particles could be magnetically separated suggesting that petrol may be a suitable replacement for diethyl ether in the first solvent composition. It is notable that the iron oxide particles cleaned according to the present example could be magnetically separated more easily than in Example 17, where only petrol was used in the first solvent composition. This goes some way to highlight the importance of combining a non-polar solvent with an appropriate flocculent and/or a low order alcohol to obtain the highest possible particle cleaning efficiency.

Figure 12:
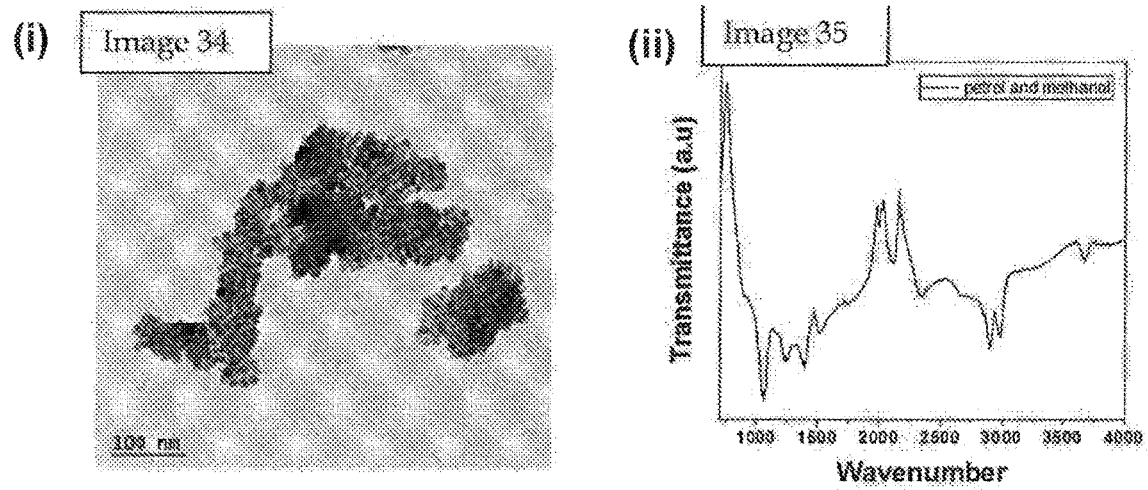
FIG. 12 shows (i) a TEM image and (ii) an FTIR spectrum of iron oxide particles purified according to the method of the preferred embodiment, in which the non-polar solvent in the first solvent composition is substituted for petrol and the flocculant is substituted for methanol.

The quality of the iron oxide particles cleaned according to the protocol of the present example would appear to be largely the same as that in Example 17, as confirmed by the TEM image (FIG. 12(i)) and the FTIR spectrum (FIG. 12(ii)) of the cleaned iron oxide particles.

Example 19—First Solvent Composition Comprising Diethyl Ether. Hexane and Methanol This present example is similar to the cleaning protocol described in Example 1, with the exception that the first solvent composition is comprised of two non-polar solvents (diethyl ether and hexane) and a flocculant (methanol) in a 1:1:2 (vol/vol) ratio.

Figure 13:
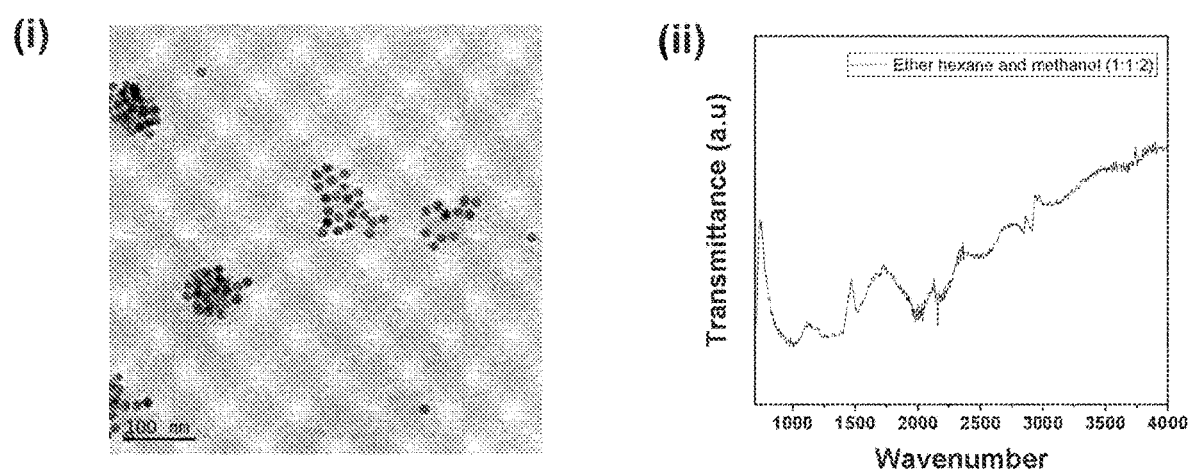
FIG. 13 shows (i) a TEM image and (ii) an FTIR spectrum of iron oxide particles purified according to the method of the preferred embodiment, in which the first solvent composition comprises two non-polar solvents (diethyl ether and hexane) and a flocculant (methanol).

The addition of hexane to the first solvent composition associated with the primary cleaning step appears to clean the particles to a high level comparable to that observed in the cleaning protocol of Example 1. Evidence for this observed improvement is apparent in the TEM image in FIG. 13(i) in which the particles appear monodispersed and well-isolated, similar to what was observed in the TEM image (FIG. 1(v)) obtained for the particles cleaned according to the protocol of Example 1. The FTIR spectrum (FIG. 13(ii)) demonstrates a significant reduction in the number of organic molecules present on the particle surface. The major changes are noted in the 1200-1600 $cm^{-1}$ vibrational range, such that the asymmetric and symmetric vibrations of metal carboxylates were observed at 1397 and 1524 $cm^{-1}$. This shifts the wavenumber separation ($\Delta_{\nu 0}$) between the $\nu_a(COO^-)$ and $\nu_s(COO^-)$ IR bands from 86 $cm^{-1}$ (as observed in respect of the cleaning protocol of Example 1) to 127 $cm^{-1}$ in the protocol of Example 19. This means that the nature of coordination of the COO group to the metal ion changes from bidentate chelating to a predominantly bridging ligand configuration. This indicates the change in the nature of bonding between iron oxide particles and oleate species from covalent towards ionic and hydrogen bonding. Considering that the strength of covalent bonds is significantly higher than those of other bonds, the addition of hexane to diethyl ether and methanol in the first solvent composition associated with the primary washing step appears to loosen the layer of organic molecules bound to the particle surface.

codes 010066-85, 22004-85, 929141-85) were obtained from Mobil Oil Australia Pty Ltd and used without further purification.

References

[1] Park, J., An, K., Hwang, Y., Park, J-G., Noh, H-J., Kim, J-Y., Park, J-H., Hwang, N-M., Hyeon, T., *Nature Materials,* 2004, vol. 3, 891-895.

[2] Burdinski et al., US Patent Application No. 2013/0089740 A1.

TABLE 1

| Example | A First solvent composition (vol/vol) | Ratio of solvent to iron oxide particles | No. of washes | B Second solvent composition (vol/vol) | No. of washes | C Dispersing solvent |
|---|---|---|---|---|---|---|
| 1 | Et$_2$O/MeOH (1:1) | 49:1 | 1 | Hex/EtOH (1:1) | 1 | Hex |
| 2 | Et$_2$O/MeOH (1:1) | 49:1 | 1 | Hex/EtOH (1:1) | 2 | Hex |
| 3 | Et$_2$O/MeOH (1:1) | 49:1 | 1 | Hex/EtOH (1:1) | 4 | Hex |
| 4 | Et$_2$O/MeOH (1:1) | 49:1 | 1 | Hex/EtOH (1:1) | 6 | Hex |
| 5A | Et$_2$O/MeOH (1:1) | 48.75:1.25 | 1 | Hex/EtOH (1:1) | 1 | Hex |
| 5B | Et$_2$O/MeOH (1:1) | 48.5:1.5 | 1 | Hex/EtOH (1:1) | 1 | Hex |
| 5C | Et$_2$O/MeOH (1:1) | 48.25:1.75 | 1 | Hex/EtOH (1:1) | 1 | Hex |
| 5D | Et$_2$O/MeOH (1:1) | 48.0:2.0 | 1 | Hex/EtOH (1:1) | 1 | Hex |
| 5E | Et$_2$O/MeOH (1:1) | 47.0:3.0 | 1 | Hex/EtOH (1:1) | 1 | Hex |
| 6 | Pr$_2$O/MeOH (1:1) | 49:1 | 1 | Hex/EtOH (1:1) | 1 | Hex |
| 7 | Oct$_2$O/MeOH (1:1) | 49:1 | 1 | Hex/EtOH (1:1) | 1 | Hex |
| 8 | Ph$_2$O/MeOH (1:1) | 49:1 | 1 | Hex/EtOH (1:1) | 1 | Hex |
| 9 | Bu$^t$(Me)O/MeOH (1:1) | 49:1 | 1 | Hex/EtOH (1:1) | 1 | Hex |
| 10 | Et$_2$O/BuOH (1:1) | 49:1 | 1 | Hex/EtOH (1:1) | 1 | Hex |
| 11 | Et$_2$O | 49:1 | 1 | — | — | — |
| 12 | EtOH | 500:1 | 1 | EtOH | 10 | — |
| 13 | Hex/Me$_2$CO (1:1) | 49:1 | 1 | Hex/EtOH (1:1) | 1 | — |
| 14* | Hex/Me$_2$CO (1:2) | 30:1 | 1 | Hex/Me$_2$CO (1:2) | 3 | — |
| 15A | Hex/MeOH (1:1) | 1:1 | 1 | — | — | — |
| 15B | Hex/BuOH (1:1) | 1:1 | 1 | — | — | — |
| 16 | Hex/Et$_2$O (1:1) | 49:1 | 1 | (Hex/Et$_2$O/EtOH (1:1:1) | 1 | — |
| 17 | Petrol | 49:1 | 1 | Hex/EtOH (1:1) | 1 | — |
| 18 | Petrol/MeOH (1:1) | 49:1 | 1 | Hex/EtOH (1:1) | 1 | — |
| 19 | Et$_2$O/Hex/MeOH (1:1:2) | 49:1 | 1 | Hex/EtOH (1:1) | 1 | — |

*Heated at 50° C.

Methods and Materials

Hexane (95% purity) was obtained from RCI Labscan Ltd (Australian distributor) and used without further purification. Methanol (99.8% purity), ethanol (99.5% purity), propan-2-ol (99% purity) and diethyl ether (99.5% purity) were obtained from Chem-Supply Pty Ltd (South Australia) and used without further purification. Butanol (99.8% purity), di-n-propyl ether (99% purity), tert-butyl methyl ether (TBME) (98% purity) and di-n-octyl ether (99% purity) were obtained from Sigma Aldrich and used without further purification. Unleaded petrol grades ("petrol"); product

[3] Bronstein, L. M., Huang, X., Retrum, J., Schmucker, A., Pink, M., Stein, B. D., Dragnea, B. 2007, "Influence of iron oleate complex structure on iron oxide nanoparticle formation", *Chemistry of Materials,* 19, 3624-3632.2007.

Whenever a range is given in the specification, for example, a temperature range, a time range, or concentration range, all intermediate ranges and subranges, as well as all individual values included in the ranges given are intended to be included in the disclosure. It will be understood that any subranges or individual values in a range or subrange that are included in the description herein can be excluded from the claims herein.

Definitions

All definitions, as defined and used herein, should be understood to control over dictionary definitions, definitions in documents incorporated by reference, and/or ordinary meanings of the defined terms.

Flocculants, or flocculating agents (also known as flocking agents), are chemicals that promote flocculation by causing colloids and other suspended particles in liquids to aggregate, forming a floc.

The indefinite articles "a" and "an," as used herein in the specification, unless clearly indicated to the contrary, should be understood to mean "at least one."

The phrase "and/or," as used herein in the specification, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

While the invention has been described in conjunction with a limited number of embodiments, it will be appreciated by those skilled in the art that many alternatives, modifications and variations in light of the foregoing description are possible. Accordingly, the present invention is intended to embrace all such alternatives, modifications and variations as may fall within the spirit and scope of the invention as disclosed.

Where the terms "comprise", "comprises", "comprised" or "comprising" are used in this specification (including the claims) they are to be interpreted as specifying the presence of the stated features, integers, steps or components, but not precluding the presence of one or more other features, integers, steps or components, or group thereof.

The present application may be used as a basis or priority in respect of one or more future applications and the claims of any such future application may be directed to any one feature or combination of features that are described in the present application. Any such future application may include one or more of the following claims, which are given by way of example and are non-limiting in regard to what may be claimed in any future application.

The claims defining the invention are as follows:

1. A method of purifying a plurality of metal oxide particles produced from a synthesis process, the method comprising the step of:
   a) washing a plurality of metal oxide particles in a first solvent composition comprising:
      i) at least one aliphatic ether; and
      ii) at least one flocculant;
         wherein the at least one aliphatic ether and the at least one flocculant are in a ratio of about 1:1 (vol/vol).

2. The method according to claim 1, wherein the at least one aliphatic ether is at least partially miscible with the at least one flocculant.

3. The method according to claim 1, wherein the at least one aliphatic ether is selected from the group consisting of diethyl ether, di-n-propyl ether, tert-butyl methyl ether and di-n-octyl ether.

4. The method according to claim 1, wherein the at least one flocculant is selected from the group consisting of an alcohol, an aldehyde and a ketone.

5. The method according to claim 4, wherein the alcohol is selected from the group consisting of methanol, ethanol and n-propanol.

6. The method according to claim 1, wherein the at least one aliphatic ether is diethyl ether and the at least one flocculant is methanol.

7. The method according to claim 1, wherein the first solvent composition further comprises at least one non-polar solvent.

8. The method according to claim 7, wherein the at least one aliphatic ether and the at least one non-polar solvent are at least partially miscible with the at least one flocculant.

9. The method according to claim 7, wherein the at least one aliphatic ether, the at least one non-polar solvent and the at least one flocculant are in a 1:1:2 (vol/vol) ratio.

10. The method according to claim 1, further comprising, after step a), the step of:
    b) further washing said plurality of washed metal oxide particles in a second solvent composition comprising of:
       i) at least one non-polar solvent; and
       ii) at least one flocculant.

11. The method according to claim 10, wherein the at least one non-polar solvent is at least partially miscible with the at least one flocculant.

12. The method according to claim 10, wherein the at least one non-polar solvent and the at least one flocculant are in a 1:1 (vol/vol) ratio.

13. The method according to claim 10, wherein the at least one non-polar solvent is hexane and the at least one flocculant is ethanol.

14. The method according to claim 10, further comprising, after step a) but before step b), the step of:
    a1) separating the plurality of washed metal oxide particles from the first solvent composition using a physical separation procedure,
       wherein the physical separation procedure is selected from the group consisting of magnetic separation, centrifugation, filtration and decantation.

15. The method according to claim 10, further comprising, after step b), the step of:
    c) dispersing said plurality of further washed metal oxide particles in a third solvent composition comprising:
       i) at least one non-polar solvent.

16. The method according to claim 15, further comprising, after step b) but before step c), the step of:
    b1) separating the plurality of further washed metal oxide particles from the second solvent composition using a physical separation procedure;
       wherein the physical separation procedure is selected from the group consisting of magnetic separation, centrifugation, filtration and decantation.

17. The method according to claim 1, wherein purifying the plurality of metal oxide particles includes purifying a plurality of iron oxide particles.

18. The method according to claim 17 wherein the method comprises the steps of:
    a) washing the plurality of iron oxide particles in a first solvent composition comprising of diethyl ether and methanol in a 1:1 (vol/vol) ratio;

b) further washing said plurality of washed iron oxide particles in a second solvent composition comprising hexane and ethanol in a 1:1 (vol/vol) ratio; and c) dispersing said plurality of washed iron oxide particles in hexane.

19. A method according to claim 18 further comprising, after step a) but before step b), the step of:

a1) separating the plurality of washed iron oxide particles from the first solvent composition using a physical separation procedure; or further comprising, after step b) but before step c), the step of:

b1) separating the plurality of further washed iron oxide particles from the second solvent composition using a physical separation procedure; or further comprising steps a1) and b1).

\* \* \* \* \*